United States Patent [19]

Hunsperger et al.

[11] Patent Number: 5,523,520
[45] Date of Patent: Jun. 4, 1996

[54] MUTANT DWARFISM GENE OF PETUNIA

[75] Inventors: Mary H. Hunsperger, Gilroy; Mathilde H. Holtrop, Aromas, both of Calif.

[73] Assignee: Goldsmith Seeds Inc., Gilroy, Calif.

[21] Appl. No.: 265,483

[22] Filed: Jun. 24, 1994

[51] Int. Cl.⁶ .............................. A01H 4/00; A01H 1/02; A01H 5/00; A01H 5/10
[52] U.S. Cl. ................. 800/200; 800/255; 800/DIG. 41; 435/240.49; 47/58
[58] Field of Search ........................... 800/200, DIG. 41, 800/255; PLT./68.1; 435/240.49; 47/58.03

[56] References Cited

U.S. PATENT DOCUMENTS

| | | | |
|---|---|---|---|
| P.P. 6,899 | 7/1989 | Tsuda et al. | PLT./68.1 |
| P.P. 6,914 | 7/1989 | Tsuda et al. | PLT./681 |
| P.P. 6,915 | 7/1989 | Tsuda et al. | PLT./68.1 |

OTHER PUBLICATIONS

Bedding Plants, John W. Mastalerz (Ed.), Pennsylvania Flower Growers, 1976, pp. 252–269.
Petunia, Ken Sink (Ed.) Springer–Verlaq, 1984, pp. 34–37.
Petunia, Ken Sink (Ed.) Springer–Verlag, 1984 Chapter 15.
Evaluation of Petunia Cultivars for the Landscape in West–Central Florida, T. K. Howe, et al., Proc. FL State Hort. Soc. 105, 1992, pp. 246–251.

Ewart in *Petunia* (Sink, ed.) Springer–Verlag, Berlin, 1984 Chapter 15, pp. 180–202.

Weddle in *Bedding Plants* (Mastalerz, ed.), Pennsylvania Flower Growers, 1976, pp. 252–269.

Izhar, et al in *Petunia* (Sink, ed.) Springer–Verlag, Berlin, 1984, pp. 116–118.

*Primary Examiner*—Che S. Chereskin
*Attorney, Agent, or Firm*—Rothwell, Figg, Ernst & Kurz

[57] ABSTRACT

This invention relates to a dwarf petunia plant, seed, variety and hybrid. More specifically, the invention relates to a petunia plant having a mutant gene for dwarfism which results in the reduced plant and flower size. The invention also relates to crossing inbreds, varieties and hybrids containing the dwarf gene to produce novel types and varieties of dwarf petunia plants and flowers for ornamental purposes.

20 Claims, No Drawings

MUTANT DWARFISM GENE OF PETUNIA

FIELD OF THE INVENTION

The present invention relates to a novel dwarfism gene of petunia which results in a reduction in plant and flower size. This present invention also relates to a petunia seed, a petunia plant, a petunia variety and a petunia hybrid which contain the dwarfism gene. In addition, the present invention is directed to transferring the dwarfism gene in the petunia plant to other petunia varieties and species and is useful for producing novel types and varieties of dwarf petunia.

BACKGROUND OF THE INVENTION

Petunias have been under cultivation at least since 1870 when seeds of wild species in Argentina were collected by the French botanist Petun. Petunia hybrida is thought to have arisen from intercrossing between at least two species, Petunia axillaris and Petunia violacea, or possible Petunia inflata, while under cultivation. The resulting variation in color and flower form has exceeded that found in the parental species.

Breeding and selection for novel traits was conducted almost immediately after introduction to cultivation. The various forms now available including the single and double, multiflora and grandiflora types, were developed in the late 1800's. Pure breeding lines were first developed in the 1920's. Breeding efforts intensified during the 1950's when the first $F_1$ multiflora hybrid became commercially accepted. Virtually all commercial petunia varieties currently in use are $F_1$ hybrids.

Petunia species are primarily self pollinating. Petunia breeding in the past 30 years has focused on the performance of the plant in the pack for the bedding plant trade. A "pack" consists of a small disposable plastic, multi-celled container used for growing plants for retail sale. Packs used for petunias commonly have an individual cell soil volume of 7–8 cubic inches. Breeding emphasis has been on characteristics such as earliness, compactness, and color range, as well as performance in the garden. The popularity of petunias over the years is due in part to their ability to withstand a wide variety of conditions as well as the range of colors and types available. They have consistently been one of the top species used for bedding plant production and held the number one position for many years. They are currently second after impatiens (Impatiens wallerana).

Detailed information about petunia breeding, diseases, agronomic traits can be found in *Bedding Plants*, John W. Mastalerz (Ed.), Pennsylvania Flower Growers, 1976 and in *Petunia*, Kenneth C. Sink (Ed.), Springer-Verlag, 1984.

Single flowered grandiflora (GF) petunias are by far the most popular type. Grandifloras are distinguished from multifloras (MF) by having a larger flower and stockier plant habit. The second most popular type is the single multiflora, which has more branches and a greater ability to come back into flower after adverse weather conditions. Grandiflora and multiflora doubles share a relatively small portion of the market.

To date, there has not been a simple method of reducing the plant and flower size to a size smaller than the current commercial cultivars. It would be desirable to have new types and forms of petunia for the commercial market, especially desirable would be a reproducible method of reducing plant and flower size in commercial petunia varieties.

SUMMARY OF THE INVENTION

The present invention relates to a petunia seed, a petunia plant, a petunia flower, a petunia variety, a petunia hybrid, and a method for producing a petunia plant.

More specifically, the invention relates to a dwarfism gene which produces a petunia plant and flower which are reduced in size. Objects of the present invention also include: 1) a reduction in time between sowing and flowering, 2) an increase in length of time the plants remain commercially marketable, 3) the maintenance of a compact plant habit throughout the growing season, 4) a reduction in plant lodging when compared to current petunias marketed, and 5) normal fertility. These objects and others are met by the present invention.

The genetic factor capable of transmitting the plant and flower size reduction has been determined to be a single recessive allele. It is a feature of the present invention that this single gene may be used in and transferred among the various petunia varieties and to other species.

The present invention further relates to a method of producing the disclosed petunia plants and seeds by crossing a dwarf petunia plant of the instant invention with another petunia plant. The invention also relates to the transfer of the genetic dwarfism into other petunia plants.

DETAILED DESCRIPTION OF THE INVENTION

In order to provide an understanding of several of the terms used in the specification and claims, the following definitions are provided:

Single flowered—As used herein, single flowered means a petunia having the single corolla gene (d), consisting of five petals fused into a single corolla.

Double flowered—As used herein, double flowered means petunias having the double corolla gene (D) which produces extra petals.

Multiflora petunia—As used herein, multiflora means a petunia having the small flowered gene (g).

Grandiflora petunia—As used herein, grandiflora means a petunia having the large flowered gene (G) which results in larger flowers, wider sepals, and a heavier plant habit.

Prostrate growth habit—The term prostrate growth habit means the plant growth is predominately horizontal resulting in a plant which is greater in diameter than in height.

Mound growth habit—The term mound growth habit means plant growth is both vertical and horizontal resulting in plants approximately as tall as they are in diameter.

Compact growth habit—The term compact growth habit means plants are smaller than normal due to shortened internodes.

Plant height at first flower—This term means the total height of the plant from the soil line to the top of the flower and is measured when the first flower on the plant is fully open.

Internode length above the first flower—This term means the length of the first internode adjacent to and above the node where the first flower is attached to the plant.

The present invention is directed to developing unique plants of the petunia species.

The petunia of the present invention expresses a substantial reduction in plant and flower size. A transferrable gene which conveys this dwarf characteristic has been isolated and incorporated into other genetic backgrounds. The dwarf gene of the instant invention has also been expressed in different genetic backgrounds of petunia. To date, there is no known dwarfism in any cultivar of petunia which is similar to the amount of dwarfism of the present invention. This previously unknown dwarfism characteristic arose from breeding and research efforts which were conducted beginning in 1986.

As the term is used herein, dwarf and dwarfism is a condition wherein the plant and flowers are reduced in size by a significant amount, i.e. a 20% or more size reduction. This size reduction should not interfere with the reproductive ability of the plant. The present invention has pollen viability within the range of MF and GF lines, which range from 35% to 85% aniline blue stainable.

The instant invention is an allelic DNA genetic factor which results in a substantial reduction in size of plants and flowers in petunia species. As is shown in Tables 1, 2, and 3 the result of incorporating this dwarf gene into other genetic backgrounds is a plant that is approximately 30% smaller in height, internodes which are approximately 45% reduced in length, flowers that are approximately 35% smaller in size and leaves that are approximately 40% smaller. It is believed that these size reductions are the result of a single recessive mutant gene.

In 1986, this dwarf characteristic was observed in an inbred line 786-1-5-(4)-80 (hereinafter called "786"). The 786 line was uniquely small flowered with a compact plant habit. The dwarf characteristic was found in the $F_2$ of breeding crosses using the 786 inbred. In 1987 a number of breeding crosses were made with the dwarf plants across a range of colors. In subsequent years, $F_3$ generation plants were selfed and backcrossed once to various multiflora genotypes. $F_3$ test crosses were made with various dwarf genotypes.

The dwarf gene of the present invention generally segregates as a simple recessive allele. A few genetic backgrounds have produced 1/16 dwarf (which may imply two genes are affecting the dwarfism expression) and in only a few genetic backgrounds has the dwarfism trait not been expressed. Also, the level of dwarfing varies depending upon the genetic background. For example, as shown in Tables 1 and 2, the white and blue dwarfs tend to be taller than the other colors, which is consistent with white and blue multiflora and grandiflora types in general versus other color types.

The dwarf phenotype of the present invention, which is being referred to as a "Milliflora" (MLF) is an entirely new classification of petunias, such as the multiflora (MF) and grandiflora (GF) classifications. The genetic difference between the MF and the GF is the presence of a single dominant gene in the GF classification of plants. The difference between the MF and the MLF is the presence of the single recessive gene of the instant invention which is present in the MLF plants. The most distinguishing traits between GF and MF are that GF petunias have wider sepals, a less constricted throat, fewer branches, and larger flowers than MF petunias. These characteristics result in MF petunias having a "finer" and more delicate appearance generally than GF. In a similar manner, MLF petunias have a "finer" and more delicate appearance than do the MF petunias, with the MLF petunias having the smaller leaves and flowers as shown in Table 3.

It is standard practice in the industry to treat petunias grown in cell packs several times with a growth regulator B-9 (Alar) before flowering to reduce internode length to obtain a compact plant. Water and fertilizer are used sparingly which further reduces internode elongation. Table 4 shows the differences between a typical MLF hybrid, Dwarf Pink Blush, with the most similar hybrids available in the market, Mini Rose Star (Farmen), Pink Pearls (Clause), and Primetime Pink (Goldsmith), when the plants are grown without growth regulators or reduced water and fertilizer. Untreated MLF plant height is 7–12 cm less at first flower than untreated MF plants, making it possible to grow petunias without the use of growth regulators.

Table 5 contains data on MF plants treated in the usual manner with the growth regulator Alar. The dwarf MLF hybrid (Dwarf White) was not treated with Alar. The difference between the dwarf MLF and MF types is not as large as in Table 4, but the MLF type is still significantly reduced in plant height (2–5 cm), flower diameter (16–24 mm), and internode length (2–6 mm). Comparison of Tables 4 and 5 indicates B-9 (Alar) applied before flower development reduces internode length but not the flower diameter.

In addition to providing dwarfism to Petunia, the transfer of the recessive gene of the present invention to different genetic backgrounds has produced the associated advantageous characteristics of: 1) a reduction in time between planting and flowering 2) an increase in the length of time the plants remain commercially marketable 3) maintenance of a compact plant habit throughout the growing season 4) a reduction in lodging, and 5) normal fertility when compared to current commercial petunias.

As shown in Table 6, our MLF petunias flower about five days earlier than do the MF and GF types due in part to the fact that the MLF petunias do not need B-9 treatment to produce the desired compact habit. Flowering is slightly delayed by using B-9 and withholding water and fertilizer. For example, untreated Primetime Pink plants flowered only two days later than untreated Dwarf Pink Blush as compared to 6 days later when treated with B-9. Untreated Dwarf Pink Blush flowered at 56 days from sowing compared to 64 and 65 days, respectively for untreated Mini Rose Star and Pink Pearls.

One important feature of the instant invention is that the reduction in time between sowing and saleability allows a reduced production cost to the producer. After the plants have come into flower and the effects of the B-9 treatment have been outgrown, the MLF plants do not increase in size as rapidly and remain saleable longer than MF and GF types. This trait can be especially important during unfavorable planting weather when sales tend to be slower.

Some dwarf MLF petunia lines are completely covered with flowers in the field throughout the season. This profusion of bloom affords a degree of weather tolerance to the disease botrytis in the garden. The more "resistant" MF and GF lines are thought to simply come back into flower faster after rain rather than being more resistant to botrytis. As shown in Table 7, MLF plants also stay more compact in the garden throughout the season, and suffer less from lodging and the resulting unattractive split canopy.

As used herein, the term "plant" includes plant cells, plant protoplasts, plant cells of tissue culture from which Petunia plants can be regenerated, plant calli, plant clumps, and plant cells that are intact in plants or pans of plants such as pollen, flowers, seeds, leaves, stems, and the like. Tissue culture of Petunia is described in *Plant Culture Media*, Vol. 1, George, Putlock, and George, incorporated herein by reference.

EXAMPLES

The following examples are provided to further illustrate the present invention and are not intended to limit the invention beyond the limitations set forth in the appended claims.

Example 1

The white MLF hybrid in Table 1 is a cross between two MLF lines, 786FB-PE 877-10-1-2-4-(4)(3) by 786FB-PE877-786GB-2-1-3-4. 786FB-PE877-10-1-2-4-(4)(3) was derived by crossing the dwarf MLF 786 to a blue MF line FB, followed by selection in the F-2 for the dwarf gene. Improvement was made through a backcross to the white MF line PE877 and the gene and the white color recovered in the F-2. This was subsequently inbred for six generations with selection for desirable habit. 786FB-PE877-786GB-2-1-3-4 was derived by crossing an individual in the F-3 generation of 786FB-PE877, described above, with the MLF line 786GB-5-3-1-1-(3), followed by selection for desirable habit through the F-4. The 786GB-5-3-1-1-(3) line used in the above cross had been derived by crossing the dwarf line 786 with the MF line GB, followed by selection in the F-2 for the dwarf gene, and selfing to the F-5 generation.

Example 2

The pink MLF hybrid in Table 1 is a cross between the MLF lines 786 FFR-OBRS-1-1-3-3 by 786FFR-105P-283K-3-1-2-1. 786FFR-OBRS-1-1-3-3 was derived crossing the original 786 dwarf line with the MF line FFR, followed by recovery of the dwarf in the F-2. This line was inbred to the F-3, then crossed to the MF line OBRS to improve other horticultural traits. The dwarf habit was recovered in the F-2 then selfed to the F-4. The line 786FFR-105P-283K-3-1-2-1 was derived by crossing an F-3 plant of the 786FFR line with the MF inbred line 105P-283K. The dwarf was recovered in the F-2 with selection during selfing through the F-4.

Example 3

The red MLF hybrid in Table 1 is a cross between the MLF lines 786 FFR-HLCAR-7-2-1-2 by 786GB-FFR-RR243HH-5-1-2-1. An F-3 plant of the 786FFR type as described above was crossed with the red MF line HLCAR. The dwarf gene and red color were recovered in the F-2 with selection and selfing through the F-4. The other parent in this cross was derived by crossing an F-3 plant of 786FFR with the MF line RR243-HH, followed by selection and selfing through the F-4.

Example 4

The plum MLF hybrid in Table 1 is a cross between the MLF lines 786FB-PE 875-FR7275RS-1-2-7-2 by 786FB-FFR-RF7275-4-2-2-(3). 786FB-PE875-FR7275RS-1-2-7-2 was derived by crossing the MLF dwarf 786FB as described in Example 1 with the MF line PE875. The dwarf gene was recovered in the F-2, the line selfed to the F-3, then crossed with the MF line FR7275RS. The dwarf was recovered in the F-2 and followed by selection and selfing through the F-4. 786FB-FFR-RF7275- 4-2-2-(3) was made by crossing an F-3 plant of 786FB as described in Example 1, with the MF line FFR. The dwarf was recovered in the F-2, selfed to the F-3, and crossed to the MF line RF-7272-RS. The dwarf was recovered in the F-2 and followed by selection and selfing through the F-4.

Example 5

The blue MLF hybrid in Table 1 is a cross between the MLF lines 786FB-PE 877-786GB-2-2-8-1 by 786FB-PE877-11-1-4-3-1-2. The derivation of 786FB-PE877-786GB-2-2-8-1 is almost identical to that described above in Example 1, however different siblings were used in each of the crosses. Similarly, 786FB-PE877- 11-1-4-3-1-2 was derived from a different hybrid plant of the MLF×MF cross, 786FB ×PE877.

TABLE 1

Plant height and internode length of Multiflora (MF) 'Primetime' and small flowered dwarf Milliflora (MLF) hybrid petunias compared by color. Data is the average of five measurements taken at full maturity in 1992 on field grown plants. The interaction between type of petunia and color of flower is not significant for internode length.

| FLOWER COLOR | PLANT HEIGHT (cm) | | INTERNODE LENGTH (mm) | |
| --- | --- | --- | --- | --- |
| | MF | MLF | MF | MLF |
| White | 61 | 45 | 32 | 18 |
| Pink | 52 | 35 | 29 | 17 |
| Red | 51 | 33 | 30 | 21 |
| Plum | 62 | 30 | 42 | 21 |
| Blue | 62 | 38 | 42 | 24 |
| LSD (a < .05)* | | 3 | | 9 |
| Mean Height | 57 | 36 | 35 | 20 |
| % Overall Reduction in Size | | 35 | | 45 |

TABLE 2

Comparison of plant height and flower diameter of Multiflora (MF) 'Primetime' and typical small flowered dwarf Milliflora (MLF) petunias compared by colors. Data is the average of five measurements taken at full maturity in 1993 on field grown plants.

| FLOWER COLOR | PLANT HEIGHT (cm) | | FLOWER DIAMETER (mm) | |
| --- | --- | --- | --- | --- |
| | MF | MLF | MF | MLF |
| White | 58 | 45 | 56 | 40 |
| Pink | 51 | 41 | 56 | 46 |
| Red | 5 1 | 42 | 59 | 38 |
| Blue | 62 | 35 | 62 | 32 |
| Pink Vein | 54 | 41 | 62 | 34 |
| Crimson Vein | 57 | 41 | 66 | 45 |
| LSD (a < .05) | | 4 | | 4 |
| Mean (a < .01) | 55 | 41 | 60 | 39 |
| % Overall Reduction in Size | | 25 | | 35 |

TABLE 3

Comparison of leaf length, leaf width, and flower diameter of Multiflora (MF) 'Primetime' and typical small flowered dwarf Milliflora (MLF) hybrid petunias compared by color. Data is the average of five random measurements taken at full maturity on field grown plants in 1992.

| FLOWER COLOR | LEAF LENGTH (mm) | | LEAF WIDTH (mm) | | FLOWER DIAMETER (mm) | |
| --- | --- | --- | --- | --- | --- | --- |
| | MF | MLF | MF | MLF | MF | MLF |
| White | 28 | 23 | 16 | 14 | 63 | 36 |
| Pink | 49 | 36 | 23 | 18 | 62 | 45 |
| Red | 43 | 26 | 21 | 12 | 68 | 42 |
| Plum | 50 | 25 | 32 | 11 | 60 | 42 |
| Blue | 49 | 24 | 35 | 12 | 59 | 34 |

TABLE 3-continued

Comparison of leaf length, leaf width, and flower diameter of Multiflora (MF) 'Primetime' and typical small flowered dwarf Milliflora (MLF) hybrid petunias compared by color. Data is the average of five random measurements taken at full maturity on field grown plants in 1992.

| FLOWER COLOR | LEAF LENGTH (mm) | | LEAF WIDTH (mm) | | FLOWER DIAMETER (mm) | |
| --- | --- | --- | --- | --- | --- | --- |
| | MF | MLF | MF | MLF | MF | MLF |
| LSD (a < .01) | 8 | | 8 | | 4 | |
| Mean Difference Between MF and MLF | 17 | | 12 | | 22 | |
| Overall % Reduction in Size | 40 | | 45 | | 35 | |

TABLE 4

Comparison of dwarf hybrid Dwarf Pink Blush (MLF) to the closest related art. Comparisons were made at first flower on plants grown without any growth regulators in 2" × 2" cells in April, 1994. Data are the average of five plants. Internode Length A is the length of the internode below the node where the first flower attaches. Internode Length B is the length of the internode above the node where the first flower attaches. The values shown below are the average values for each characteristic plus or minus the standard error.

| VARIETY | PLANT HEIGHT (cm) | FLOWER DIAMETER (mm) | INTERNODE LENGTH A (mm) | INTERNODE LENGTH B (mm) |
| --- | --- | --- | --- | --- |
| Dwarf Pink Blush | 10 ± 1 | 41 ± 2 | 0.6 ± 0.4 | 11 ± 1 |
| Mini Rose Star | 22 ± 4 | 57 ± 4 | 18 ± 7 | 25 ± 2 |
| Pink Pearls | 21 ± 1 | 62 ± 3 | 17 ± 4 | 24 ± 3 |
| Primetime Pink | 17 ± 3 | 65 ± 4 | 21 ± 7 | 46 ± 7 |

TABLE 5

Plant height, flower diameter, and length of internode above first flower of petunia cultivars grown in pack containers in April, 1994. All MF varieties were treated with two applications of B-9 (Alar), Dwarf White (MLF) was untreated. Alar reduces internode length. Data is the average of five plants taken when all were in full flower 72 days after sowing. The values shown are the average values plus or minus the standard error.

| VARIETY | PLANT HEIGHT (cm) | FLOWER DIAMETER (mm) | INTERNODE LENGTH (mm) |
| --- | --- | --- | --- |
| Dwarf White (MLF) | 8 ± 1 | 42 ± 3 | 5 ± 1 |
| Farmen Mini Mix (MF) | 10 ± 2 | 58 ± 3 | 7 ± 3 |
| Pearls Mix (MF) | 13 ± 1 | 66 ± 4 | 11 ± 4 |
| Primetime White (MF) | 11 ± 1 | 66 ± 4 | 9 ± 2 |

TABLE 6

Number of days to first flower and 50% flower for typical 1) Multiflora (MF) 'Primetime' 2) Grandiflora 'Ultra'(GF), and 3) small flowered dwarf petunia Milliflora (MLF) hybrid petunias. Data shown is the average of 9 hybrids of 9 different colors of each genotype. Plants were grown in the cell packs in the spring of 1993. All MF and GF plants were treated with two applications of B-9 (Alar) before flowering to reduce plant height as is common practice, whereas the MLF plants were not treated.

| GENOTYPE | DAYS TO FIRST FLOWER | DAYS TO 50% FLOWER |
| --- | --- | --- |
| MLF | 61 | 65 |
| MF | 67 | 70 |
| GF | 68 | 70 |
| LSD (a > .05) | 3.4 | 3.4 |

TABLE 7

Percent lodged plants for Multiflora (MF) 'Primetime' and typical small flowered dwarf Milliflora (MLF) hybrid petunias are compared by color. Data was taken at full maturity in the field on plants sown at two different sowing dates in Gilroy, CA in 1993.

| FLOWER COLOR | MF | MLF |
| --- | --- | --- |
| White | 74 | 3 |
| Pink | 88 | 0 |
| Red | 100 | 45 |
| Pink Vein | 92 | 90 |
| Plum | 96 | 40 |
| Avg. | 90 | 36 |
| LSD Avg. (a < .05) | 20 | |

DEPOSIT INFORMATION

Petunia seeds have been placed on deposit with the American Type Culture Collection (ATCC), Rockville, Md. 20852, under Deposit Accession Number 75777 on May 20, 1994.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A petunia seed containing an allelic DNA genetic factor for dwarfism, wherein said seed has a pedigree which includes the plant 786-1-5-(4)-80.

2. The petunia seed of claim 1, wherein said seed contains a recessive allele for dwarfism.

3. A dwarf petunia plant produced by growing the seed of claim 1.

4. The petunia plant of claim 3, wherein said plant is a single flowered petunia.

5. The petunia plant of claim 3, wherein said plant is a double flowered petunia.

6. The petunia plant of claim 3, wherein said plant is a multiflora petunia.

7. The petunia plant of claim 3, wherein said plant is a grandiflora petunia.

8. The petunia plant of claim 3, wherein said plant has a prostrate growth habit.

9. The petunia plant of claim 3, wherein said plant has a mound growth habit.

10. The petunia plant of claim 3, wherein said plant has a compact growth habit.

11. The petunia plant of claim 3, wherein said plant has a spreading growth habit.

12. Pollen of the plant of claim 3.

13. An ovule of the plant of claim 3.

14. A tissue culture comprising regenerable cells of the plant of claim 3.

15. A petunia plant regenerated from said tissue culture of claim 14.

16. A method for producing $F_1$ hybrid petunia seed comprising crossing a first parent petunia plant with a second parent petunia plant and harvesting the resultant $F_1$ hybrid petunia seed, wherein said first or second parent petunia plant is the petunia plant of claim 3.

17. The method of claim 16, wherein said petunia plant of claim 3 is the female plant.

18. The method of claim 16, wherein said petunia plant of claim 3 is the male plant.

19. A first generation ($F_1$) hybrid petunia plant produced by growing said hybrid petunia seed of claim 16.

20. Viable petunia seeds and plants and succeeding generations thereof grown from seeds deposited under ATCC Accession No. 75777 and petunia seeds and plants to which the dwarfism allele is transferred from said deposited seeds in succeeding generations thereof.

* * * * *